United States Patent
Wakai et al.

(10) Patent No.: US 7,221,729 B2
(45) Date of Patent: May 22, 2007

(54) X-RAY COMPUTER TOMOGRAPHY APPARATUS

(75) Inventors: Misako Wakai, Nasushiobara (JP); Shinsuke Tsukagoshi, Nasushiobara (JP); Tatsuo Maeda, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/401,936

(22) Filed: Apr. 12, 2006

(65) Prior Publication Data

US 2006/0233296 A1  Oct. 19, 2006

(30) Foreign Application Priority Data

Apr. 15, 2005 (JP) .............................. 2005-118769

(51) Int. Cl.
*A61B 6/00* (2006.01)
*H05G 1/38* (2006.01)
*H05G 1/44* (2006.01)

(52) U.S. Cl. .............................. 378/8; 378/15; 378/96; 378/108

(58) Field of Classification Search .................... 378/4, 378/5, 8, 15, 19, 96, 108–114, 901
See application file for complete search history.

(56) References Cited

U.S. PATENT DOCUMENTS

| | | | |
|---|---|---|---|
| 5,301,672 A | * | 4/1994 | Kalender .................... 600/428 |
| 6,337,992 B1 | * | 1/2002 | Gelman ....................... 600/425 |
| 6,876,720 B2 | | 4/2005 | Tsuyuki |
| 6,888,914 B2 | * | 5/2005 | Edic ................................ 378/4 |
| 6,922,462 B2 | * | 7/2005 | Acharya et al. .......... 378/98.11 |
| 7,042,975 B2 | * | 5/2006 | Heuscher ........................ 378/8 |
| 7,065,395 B2 | * | 6/2006 | Lienard et al. .............. 600/431 |
| 7,082,180 B2 | * | 7/2006 | Edic et al. ....................... 378/4 |

FOREIGN PATENT DOCUMENTS

JP  2003-245275  9/2003

* cited by examiner

*Primary Examiner*—Edward J. Glick
*Assistant Examiner*—Irakli Kiknadze
(74) *Attorney, Agent, or Firm*—Oblon, Spivak, McClelland, Maier & Neustadt, P.C.

(57) ABSTRACT

An X-ray computer tomography apparatus which performs prep scanning prior to main scanning to acquire information for use in reconstruction of a tomographic image for diagnosis, the main scanning including rotary scanning around a rotation axis, and axial scanning along the rotation axis, the X-ray computer tomography apparatus includes determination unit which determines a speed based on a change of a characteristic amount concerning information obtained by the prep scanning, and a unit which controls, to the determined speed, a speed of the axial scanning in a period from the start to the completion of the main scanning.

10 Claims, 4 Drawing Sheets

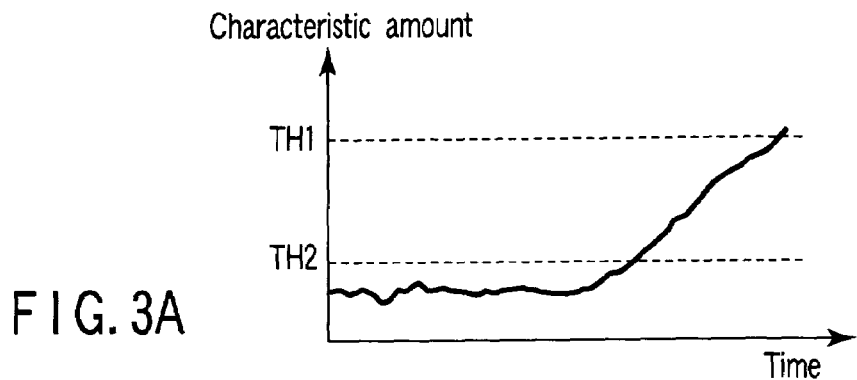
FIG. 3A
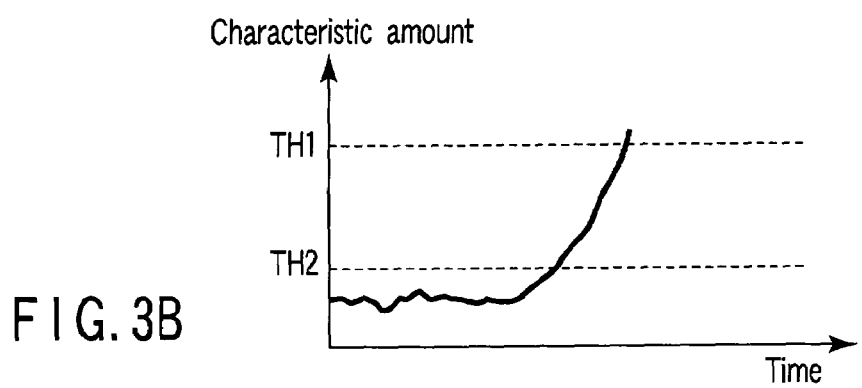
FIG. 3B
| Velocity of blood flow | Slice thickness | No. of rows | Helical pitch | Movement amount |
|---|---|---|---|---|
| S1 | 1mm | 64 rows | 53 | 53mm/rot |
| S2 | 1mm | 32 rows | 27 | 27mm/rot |
| S3 | 1mm | 16 rows | 15 | 15mm/rot |
| S4 | 1mm | 8 rows | 7.5 | 7.5mm/rot |
| S5 | 1mm | 4 rows | 3.5 | 3.5mm/rot |
FIG. 4

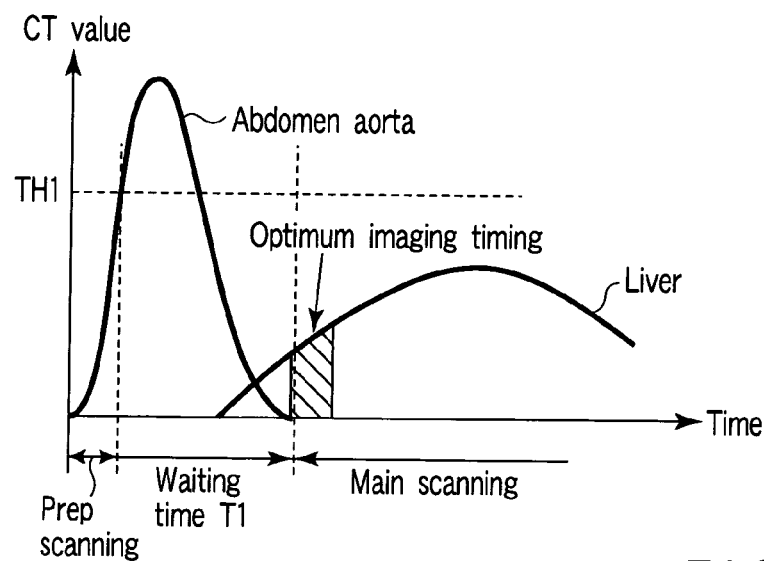
| Velocity of blood flow | Waiting time |
|---|---|
| S11 | 0 second |
| S12 | 5 seconds |
| S13 | 10 seconds |
| S14 | 15 seconds |
| S15 | 20 seconds |
FIG. 5
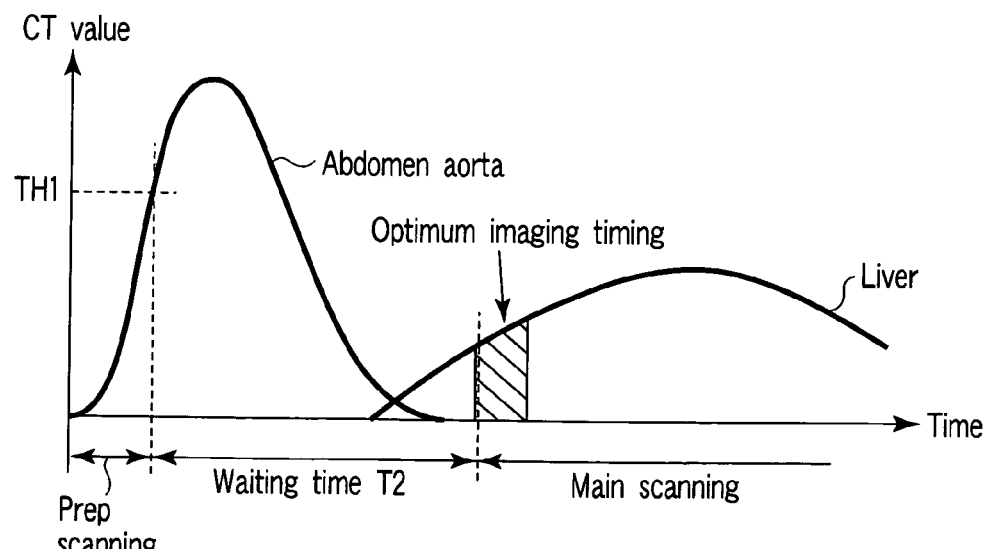
FIG. 6A
FIG. 6B

X-RAY COMPUTER TOMOGRAPHY APPARATUS

CROSS-REFERENCE TO RELATED APPLICATIONS

This application is based upon and claims the benefit of priority from prior Japanese Patent Application No. 2005-118769, filed Apr. 15, 2005, the entire contents of which are incorporated herein by reference.

BACKGROUND OF THE INVENTION

1. Field of the Invention

The present invention relates to an X-ray computer tomography apparatus which obtains a tomographic image of a subject by use of an X-ray.

2. Description of the Related Art

In a case where a contrast medium is utilized in an X-ray computer tomography apparatus, it is important to perform main scanning at a timing when the contrast medium administered to a subject flows into a portion (portion to be imaged) from which a tomographic image is to be obtained. The main scanning is scanning which collects data to reconstruct the tomographic image for diagnosis.

In Jpn. Pat. Appln. KOKAI Publication No. 2003-245275, a technology is disclosed in which preparatory scanning (prep scanning) is performed before the main scanning, an inflow situation of the contrast medium into the portion to be imaged is monitored based on a change of a CT value measured by this prep scanning, and the main scanning is automatically started in accordance with the monitored situation.

In general, the prep scanning is performed with respect to an object which is a portion different from the portion to be imaged. For example, in a case where the portion to be imaged is a liver, the prep scanning is performed with respect to an abdomen aorta as the object. Therefore, the main scanning is started with elapse of a certain time after the CT value measured by the prep scanning exceeds a threshold value, in order to wait until the contrast medium sufficiently flows into the portion to be imaged.

However, there is an individual difference in a time required for the contrast medium to reach the portion to be imaged from the portion which is the object of the prep scanning. Therefore, when the waiting time required until the main scanning is started is set to be constant as described above, there is a case where the main scanning is not started at an optimum timing.

Additionally, when axial scanning is performed along a rotation axis in addition to rotary scanning around the rotation axis during helical scanning or the like, a broad region is photographed in a direction along the rotation axis. To perform such tomography, even in a case where the main scanning is started at an appropriate timing, unless the axial scanning is performed at an appropriate speed during the main scanning, the portion to be imaged deviates from a bolus peak of the contrast medium, and the main scanning might not be appropriately performed.

In U.S. Pat. No. 6,337,992, a technology is disclosed in which a curve indicating a change of an X-ray decay value is estimated based on the change of the X-ray decay value immediately after starting injection of the contrast medium, and the helical scanning is started at a time when this curve is expected to come close to its maximum.

However, a step of estimating the above-described curve is very complicated, and it is difficult to achieve high precision. Therefore, if this curve has a large error, the timing to start the helical scanning might deviate from an optimum timing.

BRIEF SUMMARY OF THE INVENTION

Such circumstances have demanded that main scanning should be performed at an appropriate timing when the vicinity of a bolus peak of a contrast medium passes over the whole tomography region.

According to a first aspect of the present invention, there is provided an X-ray computer tomography apparatus which performs prep scanning prior to main scanning to acquire information for use in reconstruction of a tomographic image for diagnosis, the main scanning including rotary scanning around a rotation axis, and axial scanning along the rotation axis, the X-ray computer tomography apparatus comprising: determination unit which determines a speed based on a change of a characteristic amount concerning information obtained by the prep scanning; and a unit which controls, to the determined speed, a speed of the axial scanning in a period from the start to the completion of the main scanning.

According to a second aspect of the present invention, there is provided an X-ray computer tomography apparatus which performs prep scanning prior to main scanning to acquire information for use in reconstruction of a tomographic image for diagnosis, the main scanning including rotary scanning around a rotation axis, and axial scanning along the rotation axis, the X-ray computer tomography apparatus comprising: a determination unit which determines a timing to start the main scanning based on an inclination of a change of a characteristic amount with time concerning information obtained by the prep scanning; and a unit which controls the X-ray computer tomography apparatus to start the main scanning at the determined timing.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3A, 3B are diagrams showing one example of a curve indicating a change of a CT value with time;

FIG. 4 is a diagram showing one example of a table showing a relation between a velocity of blood flow and main scanning conditions;

FIG. 5 is a diagram showing one example of a table showing a relation between the velocity of blood flow and waiting time; and FIG. 6A, 6B are diagrams showing a change of a CT value with time in each of an abdomen aorta and a liver, and showing timings to execute prep scanning and main scanning.

DETAILED DESCRIPTION OF THE INVENTION

There will be described hereinafter an X-ray computer tomography apparatus (X-ray CT apparatus) of the present invention with reference to the drawings.

Figure 1:
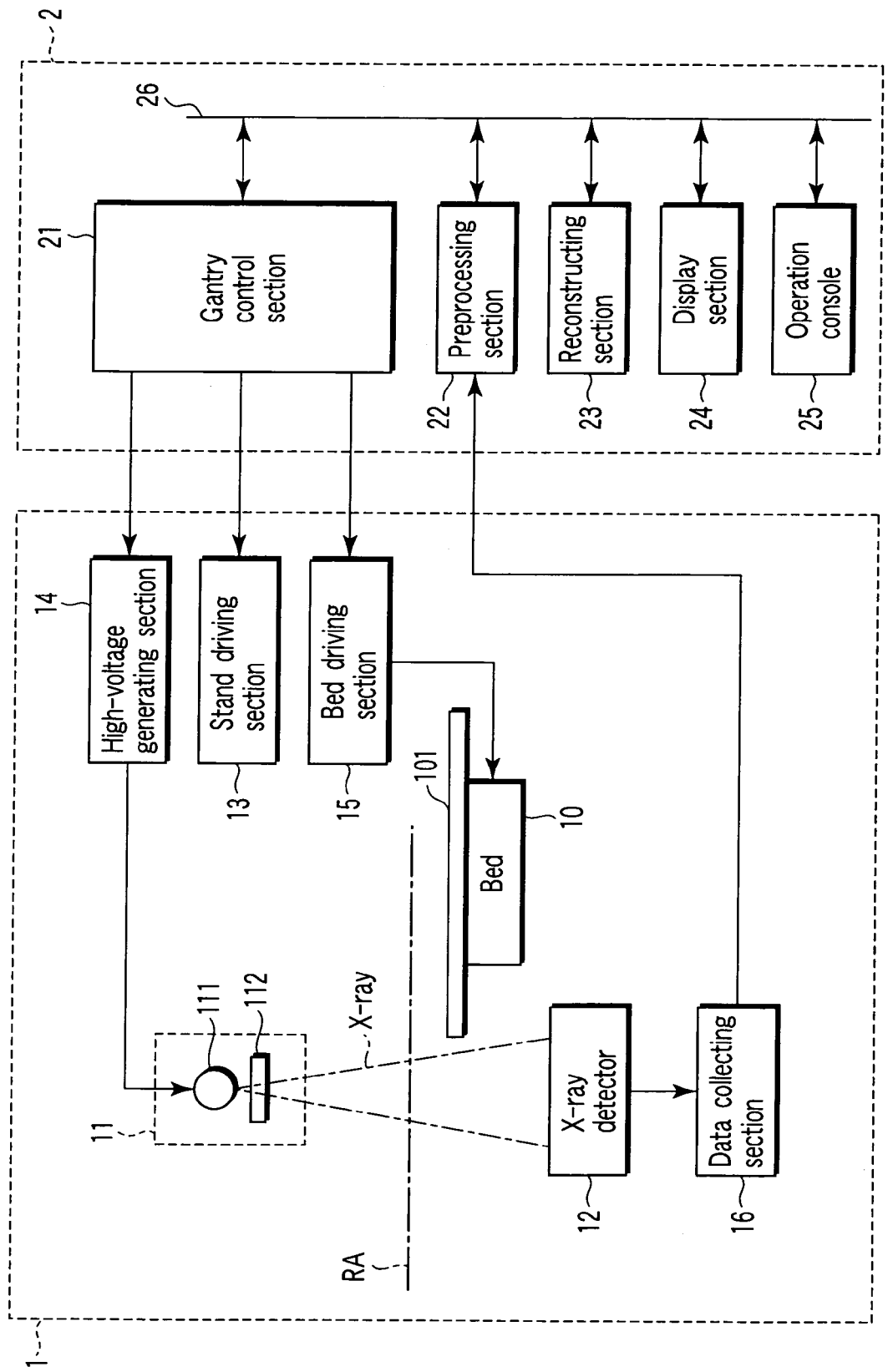
FIG. 1 is a diagram showing a constitution of a main part of an X-ray CT apparatus in one embodiment of the present invention.

FIG. 1 is a diagram showing a constitution of a main part of the X-ray CT apparatus in the present embodiment. In the present embodiment, the X-ray CT apparatus includes a scanning gantry 1 and a computer device 2. The scanning gantry 1 is a constituting element for collecting projection data on a subject. The projection data collected by the scanning gantry 1 is for use in processing such as image reconstruction and prep processing in the computer device 2. It is to be noted that the prep processing indicates processing for automatically starting main scanning based on results of prep scanning as described later.

The scanning gantry 1 includes a bed 10, an X-ray tube device 11, an X-ray detector 12, a stand driving section 13, a high-voltage generating section 14, a bed driving section 15, and a data collecting section 16.

In the scanning gantry 1, the X-ray tube device 11 and the X-ray detector 12 are attached to an annular rotary stand to face each other. The rotary stand is rotated by the stand driving section 13. At this time, the X-ray tube device 11 and the X-ray detector 12 rotate around the same rotation axis RA. In the scanning gantry 1, a hollow is formed in a rotation track of the X-ray tube device 11 and the X-ray detector 12.

The X-ray tube device 11 includes an X-ray tube 111 and an X-ray filter 112. The X-ray tube 111 receives a power supply from the high-voltage generating section 14, and emits an X-ray toward the X-ray detector 12. The X-ray filter 112 removes a low energy component from the X-ray emitted from the X-ray tube 111 in order to reduce radiation exposure. The high-voltage generating section 14 includes a high-voltage transformer, a filament current generator, and a rectifier. Additionally, the high-voltage generating section 14 includes a tube voltage switching unit, a filament current switching unit and the like in order to adjust a tube voltage and a filament current arbitrarily or in stages.

The X-ray detector 12 is constituted by arranging a plurality of X-ray detecting element rows in a direction along the rotation axis RA. The X-ray detector 12 detects an incident X-ray, and outputs an electric signal in accordance with an intensity of the ray.

A subject is laid on a top plate 101 of the bed 10. The bed 10 is driven by the bed driving section 15, and the top plate 101 is moved in a longitudinal direction (left and right direction in FIG. 1). The bed 10 is usually disposed so that the longitudinal direction is parallel to the rotation axis RA. The subject is usually laid on the top plate 101 so that a body axis of the subject extends along the rotation axis RA. Therefore, the subject is inserted into the hollow of the scanning gantry 1 with movement of the top plate 101.

The data collecting section 16 collects an output of the X-ray detector 12, and supplies the output to the computer device 2. It is to be noted that an interface using a slip ring or optical communication is inserted between the X-ray detector 12 and the data collecting section 16. Accordingly, the data collecting section 16 can collect the output of the X-ray detector 12 while continuously rotating the rotary stand.

The computer device 2 includes a gantry control section 21, a preprocessing section 22, a reconstructing section 23, a display section 24, and an operation console 25. These gantry control section 21, preprocessing section 22, reconstructing section 23, display section 24, and operation console 25 are connected to one another via a bus 26.

Data supplied from the scanning gantry 1 to the computer device 2 is supplied as the projection data to the reconstructing section 23 via the preprocessing section 22. The reconstructing section 23 reconstructs tomographic image data based on the projection data. The tomographic image data is displayed in the display section 24, supplied to the gantry control section 21, and used in the prep processing.

The operation console 25 is disposed for an operator to input various information or instructions such as main scanning conditions and prep processing conditions. The operation console 25 includes an operation screen.

The gantry control section 21 controls an operation of the scanning gantry 1 to perform the prep scanning or the main scanning. The gantry control section 21 further includes the following functions: a first function of judging the velocity of blood flow based on an image obtained by the prep scanning; a second function of determining a waiting time from the completion of the prep scanning to the start of the main scanning based on the judged velocity of blood flow; a third function of outputting a guidance concerning the main scanning synchronously with a start timing of the main scanning determined by the above waiting time; a fourth function of determining a scanning speed in the direction along the rotation axis RA during the main scanning, that is, a moving speed of the top plate 101 based on the judged velocity of blood flow; a fifth function of setting the moving speed of the top plate 101 during the main scanning to the speed determined as described above; and a sixth function of changing an information collecting density per unit time in the direction along the rotation axis RA in accordance with the moving speed of the top plate 101 during the main scanning.

Next, there will be described an operation of an X-ray CT apparatus constituted as described above.

Figure 2:
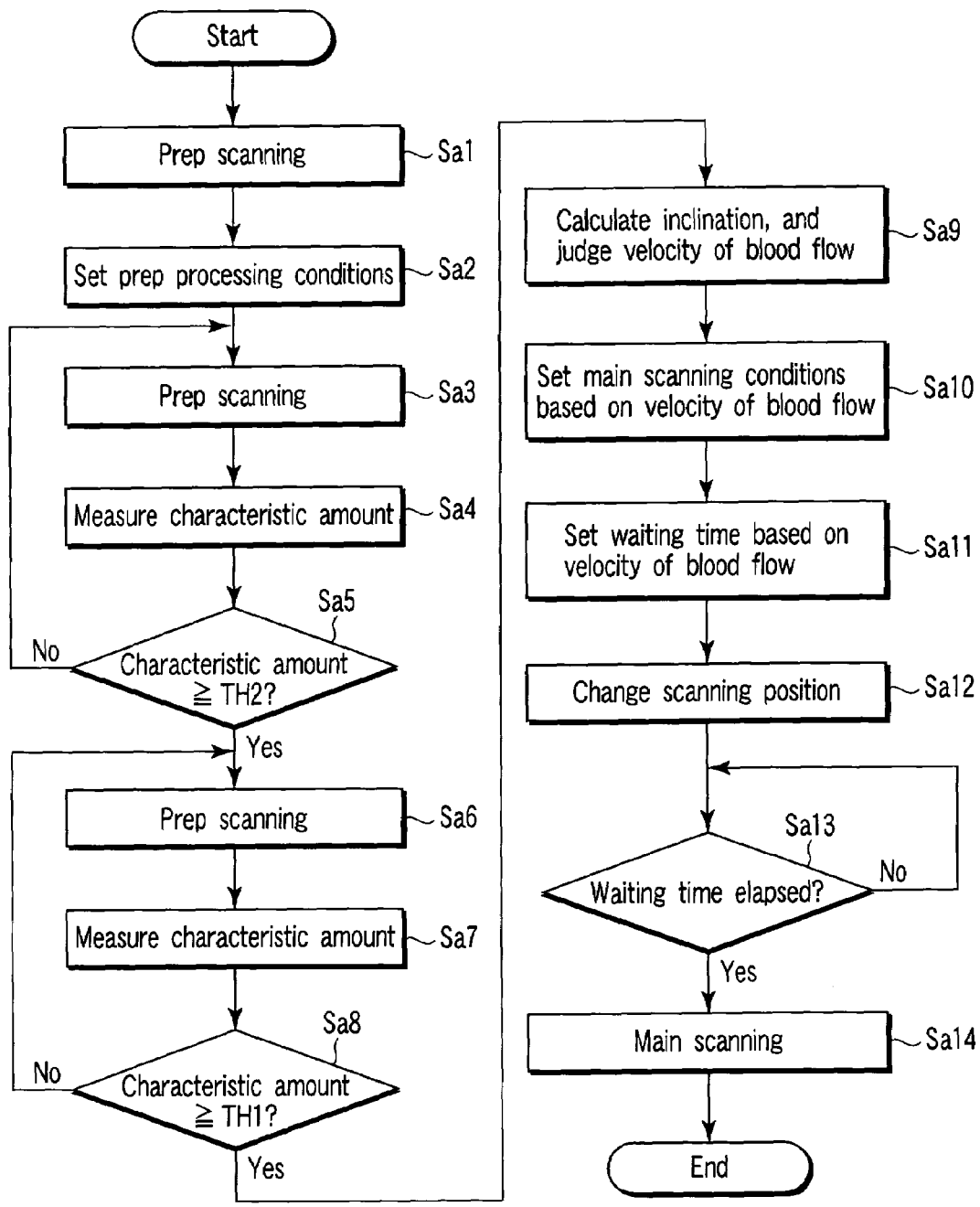
FIG. 2 is a flowchart showing a processing procedure of a gantry control section in FIG. 1.

FIG. 2 is a flowchart showing a processing procedure of the gantry control section 21 in FIG. 1. Prior to starting of processing shown in FIG. 2, the gantry control section 21 positions a slice, and sets prep scanning conditions (tube voltage, tube current, scanning time, bundled channel number, helical pitch, etc.), main scanning conditions (tube voltage, tube current, scanning time, bundled channel number, imaging region, etc.) and the like based on user's operation. It is to be noted that the gantry control section 21 takes scanogram to determine a imaging region.

In step Sa1, the gantry control section 21 operates the scanning gantry 1 to perform prep scanning of one slice. At this time, injection of the contrast medium is not started. The data collected by the data collecting section 16 during the prep scanning is preprocessed by the preprocessing section 22, and reconstructed by the reconstructing section 23. By carrying out the prep scanning repeatedly as described later, a fluoroscopic image (moving CT image) is obtained. Known processing is usable in the preprocessing and reconstruction processing. The gantry control section 21 displays a reconstructed image (hereinafter referred to as a prep scanned image) obtained by the reconstructing section 23 in the display section 24. Moreover, in step Sa2, the gantry control section 21 sets prep processing conditions (ROI, threshold value TH1, waiting time, etc.) based on the user's operation and the like.

Thereafter, an injector is synchronized, and the injection of the contrast medium into the subject is started.

In step Sa3, the gantry control section 21 operates the scanning gantry 1 to perform the prep scanning of one slice. In step Sa4, the gantry control section 21 measures a characteristic amount based on a state of the ROI in the prep scanned image obtained during the prep scanning. It is to be noted that the ROI is generally set so that a plurality of pixels are included. In this case, the gantry control section 21 may use, as a characteristic value of the ROI, a CT value of one representative pixel (e.g., pixel positioned in the center of the ROI) among a plurality of pixels included in the ROI), or the gantry control section may obtain the characteristic amount based on the CT values of a plurality of pixels. In the latter case, for example, an average value or an added value of the CT values of a plurality of pixels may be used as the characteristic amount. Even in a case where the characteristic amount is obtained by any of the above methods, a difference value between the CT value before imaging and the CT value after imaging in each pixel may be used instead of the CT value after imaging of each pixel.

In step Sa5, the gantry control section 21 confirms whether or not the measured characteristic amount is smaller than a threshold value TH2. The threshold value TH2 is set to be smaller than the threshold value TH1 so that it is detected that the CT value starts rising in a case where the contrast medium reaches the ROI. The threshold value TH2 may be fixed, or set to a value having a certain relation with the characteristic amount at a time when the prep scanning starts or the threshold value TH1.

When the characteristic amount is smaller than the threshold value TH2, the gantry control section 21 returns from the step Sa5 to the step Sa3, and repeats the steps Sa3 to Sa5. Moreover, when the characteristic amount rises to the threshold value TH2, the gantry control section 21 advances from the step Sa5 to Sa6.

In a processing loop of steps Sa6 to Sa8, the gantry control section 21 repeatedly performs the prep scanning and the measurement of the characteristic amount. When the characteristic amount rises above the threshold value TH1, the gantry control section 21 advances from the step Sa8 to Sa9, and goes out of this processing loop.

In the step Sa9, the gantry control section 21 calculates an inclination of a change of the characteristic amount, and judges a velocity of blood flow based on this calculated inclination. That is, in a case where the velocity of blood flow is comparatively low, the characteristic amount moderately rises as shown in FIG. 3A. On the other hand, in a case where the velocity of blood flow is comparatively high, the characteristic amount rapidly rises as shown in FIG. 3B. Therefore, the gantry control section 21 calculates the inclination of the change of the characteristic amount from the threshold value TH2 to the threshold value TH1 based on a time required from a time when the characteristic amount reaches the threshold value TH2 until the amount reaches the threshold value TH1, and a difference between the threshold value TH1 and the threshold value TH2.

A property of the change of the characteristic amount is not linear as shown in FIG. 3A or 3B. However, here an average inclination is calculated in a period from a time when the characteristic amount reaches the threshold value TH2 until the amount reaches the threshold value TH1. The inclination obtained in this manner is substantially proportional to the velocity of blood flow. Therefore, the gantry control section 21 judges the velocity of blood flow based on the calculated inclination. It is to be noted that here the velocity of blood flow is judged to be any of five stages S1 to S5, and judged to be any of five stages S11 to S15. Among the blood flow velocities S1 to S5, the blood flow velocity S1 is highest, and the blood flow velocity S5 is lowest. Among the blood flow velocities S11 to S15, the blood flow velocity S11 is highest, and the blood flow velocity S15 is lowest. It is to be noted that S1 to S5 are different from S11 to S15 in a range of each division.

In step Sa10, the gantry control section 21 sets the main scanning conditions based on the above-described judged blood flow velocities S1 to S5. In a case where the main scanning is performed by helical scanning which is a combination of rotary scanning by rotating of the X-ray tube device 11 and the X-ray detector 12 with axial scanning by moving of the top plate 101 in an axial direction of the rotation axis RA, the main scanning conditions are set with reference to a table shown in FIG. 4, with the proviso that the main scanning conditions are determined so that at least an axial scanning speed, that is, movement of the top plate 101 increases when the velocity of blood flow becomes high. Furthermore, the movement of the top plate 101 is preferably determined so that the movement agrees with that of the contrast medium at each velocity of blood flow as much as possible. In addition, in the present embodiment, as shown in FIG. 4, the number of rows from which the data is to be collected is set to increase when the movement amount of the top plate 101 increases. Accordingly, resolution is uniformed in the direction along the rotation axis RA.

In step Sa11, the gantry control section 21 sets the waiting time based on the velocity of blood flow judged as described above. The waiting time can be set with reference to a table shown in, for example, FIG. 5. This table can be prepared based on results of, for example, experiments and simulations. It is to be noted that an appropriate waiting time at a certain velocity of blood flow changes with a relation between a portion as a main scanning object and a portion as a prep scanning object. To solve the problem, tables are prepared beforehand with respect to a plurality of combinations of the portions as the main scanning objects with the portions as the prep scanning objects, and these tables are appropriately selected, which is convenient.

In step Sa12, the gantry control section 21 changes a position to be scanned from the object portion of the prep scanning to that of the main scanning. In addition, in step Sa13, the gantry control section 21 waits until the waiting time set in the step Sa11 elapses from a time when it is confirmed in the step Sa8 that the characteristic amount reaches or exceeds the threshold value TH1. Furthermore, when the waiting time elapses, the gantry control section 21 advances from the step Sa13 to Sa14.

In the step Sa14, the gantry control section 21 operates the scanning gantry 1 to perform the main scanning on the conditions set beforehand and those set in the step Sa10. It is to be noted that an operation of the main scanning may be similar to that a conventional apparatus of the same type. Moreover, when the imaging of the designated imaging region is completed, the gantry control section 21 completes the processing shown in FIG. 2.

Additionally, the gantry control section 21 outputs a guidance such as a voice guidance concerning the main scanning at a timing synchronized with the main scanning start timing which is determined by the timing when it is confirmed in the step Sa8 that the characteristic amount reaches or exceeds the threshold value TH1 and by the waiting time set in the step Sa11. That is, the section outputs the guidance at a timing before or after the elapse of a certain time from the main scanning start timing.

As described above, according to the present embodiment, the velocity of blood flow is judged during the prep scanning, and the top plate 101 is moved faster as this velocity of blood flow increases during the main scanning. Since the contrast medium moves together with blood, the speed of the contrast medium is high as the velocity of blood flow increases. Therefore, when the moving speed of the top plate 101 is adjusted based on the velocity of blood flow as described above, the moving speed of the contrast medium can be brought close to an axial scanning speed. Therefore, the vicinity of the bolus peak can be imaged over the whole imaging region, and efficient imaging can be performed. Needless to say, this improves an image quality. Moreover, as long as a standard image quality is obtained, an amount of the contrast medium to be injected or an amount of exposure to the X-ray can be reduced, and a burden imposed on the subject can be reduced.

Moreover, an optimum imaging timing changes with the velocity of blood flow, but according to the present embodiment, the waiting time is changed in accordance with the velocity of blood flow. Accordingly, as shown in FIG. 6A, 6B, the main scanning can be performed at the optimum imaging timing. It is to be noted that FIG. 6A, 6B show a change of a CT value with time in each of an abdomen aorta as the prep scanning object portion and a liver as the main scanning object portion, and show timings to execute the prep scanning and the main scanning. Moreover, FIG. 6A shows a situation in which the velocity of blood flow is higher than that of FIG. 6B.

Furthermore, according to the present embodiment, an average inclination of the change of the characteristic amount with time from the threshold value TH2 to TH1 is considered in order to determine the timing to start the main scanning. Therefore, processing is easier than that of a technology disclosed in U.S. Pat. No. 6,337,992. In addition, the start timing can be determined securely.

In this embodiment, the following various modifications are possible.

The inclination of a change of the characteristic amount may be obtained by a method different from the method used in the above embodiment.

The moving speed of the top plate 101 or the waiting time may be set based on the time required from the time when the characteristic amount reaches the threshold value TH2 until the amount reaches a third threshold value which is smaller than the threshold value TH1.

The inclination may be calculated based on the change of the characteristic amount in a period from the time when the characteristic amount reaches the threshold value TH2 until the certain time elapses.

The collecting row number does not have to be changed in accordance with the velocity of blood flow. Instead of changing the collecting row number, a slice thickness may be changed in accordance with the velocity of blood flow, or both of the collecting row number and the slice thickness may be changed in accordance with the velocity of blood flow. Alternatively, a parameter other than these parameter may be changed in accordance with the velocity of blood flow.

The main scanning may be started in response to a start instruction given by a user based on a prep-scanned image instead of automatically starting the main scanning. In this case, when the waiting time set in the step Sa11 is displayed, the user can recognize the optimum timing to start the main scanning. Moreover, the user can easily instruct the start at an appropriate timing.

Instead of judging the velocity of blood flow based on the inclination of the change of the characteristic amount, the moving speed of the top plate 101 or the waiting time may be set directly from the inclination of the change of the characteristic amount.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computer tomography apparatus which performs prep scanning prior to main scanning to acquire information for use in reconstruction of a tomographic image for diagnosis, the X-ray computer tomography apparatus comprising:
    a determination unit which determines a speed based on a change of a characteristic amount concerning information obtained by the prep scanning; and
    a unit which controls, to the determined speed, a speed of an axial scanning in a period from the start to the completion of the main scanning.

2. The X-ray computer tomography apparatus according to claim 1, wherein the determination unit determines the speed based on an average inclination of the change of the characteristic amount in a predetermined period.

3. The X-ray computer tomography apparatus according to claim 2, wherein the determination unit judges a velocity of blood flow based on the inclination to determine the speed based on the velocity of blood flow.

4. The X-ray computer tomography apparatus according to claim 1, further comprising:
    a unit which changes an information collecting density per unit time during the axial scanning in accordance with the determined speed.

5. The X-ray computer tomography apparatus according to claim 1, wherein the characteristic amount is one of an average value of a plurality of CT values obtained concerning a plurality of pixels in an interest region by the prep scanning; an added value of the plurality of CT values; an average value of difference values between the plurality of CT values and a CT value obtained from the same pixel before injecting of a contrast medium is started; and an added value of the difference values between the plurality of CT values and the CT value obtained from the same pixel before the injecting is started.

6. An X-ray computer tomography apparatus which performs prep scanning prior to main scanning to acquire information for use in reconstruction of a tomographic image for diagnosis, the X-ray computer tomography apparatus comprising:
    a determination unit which determines a timing to start the main scanning based on an inclination of a change of a characteristic amount with time concerning information obtained by the prep scanning; and
    a unit which controls the X-ray computer tomography apparatus to start the main scanning at the determined timing.

7. The X-ray computer tomography apparatus according to claim 6, wherein the determination unit determines the timing based on an average inclination of the change of the characteristic amount in a predetermined period.

8. The X-ray computer tomography apparatus according to claim 6, wherein the determination unit judges a velocity of blood flow based on the inclination to determine the timing based on the velocity of blood flow.

9. The X-ray computer tomography apparatus according to claim 6, wherein the characteristic amount is one of an average value of a plurality of CT values obtained concerning a plurality of pixels in an interest region by the prep scanning; an added value of the plurality of CT values; an average value of difference values between the plurality of CT values and a CT value obtained from the same pixel before injecting of a contrast medium is started; and an added value of the difference values between the plurality of CT values and the CT value obtained from the same pixel before the injecting is started.

10. The X-ray computer tomography apparatus according to claim 6, further comprising:
a unit that outputs a guidance concerning the main scanning synchronously with the start of the main scanning at the determined timing.

\* \* \* \* \*